(12) United States Patent
Oien et al.

(10) Patent No.: US 9,474,584 B2
(45) Date of Patent: Oct. 25, 2016

(54) DENTAL INSTRUMENT SERVICING SYSTEM

(75) Inventors: Hal J. Oien, Tualatin, OR (US); James B. Johnsen, Beaverton, OR (US)

(73) Assignee: Jordco, Inc., Beaverton, OR (US)

( * ) Notice: Subject to any disclaimer, the term of this patent is extended or adjusted under 35 U.S.C. 154(b) by 960 days.

(21) Appl. No.: 12/726,208

(22) Filed: Mar. 17, 2010

(65) Prior Publication Data

US 2011/0229843 A1 Sep. 22, 2011

(51) Int. Cl.
*A61C 13/38* (2006.01)
*A61C 5/02* (2006.01)
*A61C 19/00* (2006.01)

(52) U.S. Cl.
CPC .............. *A61C 5/025* (2013.01); *A61C 19/002* (2013.01); *A61C 19/006* (2013.01)

(58) Field of Classification Search
CPC .......... A61C 3/00; A61C 3/04; A61C 19/00; A61C 19/006; A61C 5/025; A61C 19/002
USPC ........... 33/513, 514; 132/320; 223/106, 108, 223/109 R; 433/25, 72, 75, 77, 102, 165, 433/229; 606/148
See application file for complete search history.

(56) References Cited

U.S. PATENT DOCUMENTS

| | | | |
|---|---|---|---|
| 199,040 A | 1/1878 | Doak | |
| 538,482 A | 4/1895 | Doan et al. | |
| 574,031 A | 12/1896 | Hakins | |
| 711,340 A | 10/1902 | Paynter | |
| 745,833 A | 12/1903 | Hanson | |
| 750,574 A | 1/1904 | Bicket | |
| 810,292 A | 1/1906 | Meaker | |
| 895,124 A | 8/1908 | Sundee | |
| 897,822 A | 9/1908 | Dougherty | |
| 902,109 A | 10/1908 | Powell | |
| 983,993 A | 2/1911 | Graef | |
| 1,104,650 A | 7/1914 | Fries | |
| 1,287,926 A | 12/1918 | Ecaubert | |
| 1,357,063 A | 10/1920 | Korb | |
| 2,166,835 A | 7/1939 | Yancey | |
| 2,222,741 A | 11/1940 | Bush | |
| 2,286,292 A | 6/1942 | Mall | |
| 2,340,024 A | 1/1944 | Skaller | |
| 2,394,882 A | 2/1946 | Weynand | |
| 2,398,664 A | 4/1946 | Paul | |

(Continued)

FOREIGN PATENT DOCUMENTS

| | | |
|---|---|---|
| DE | 672565 | 3/1939 |
| FR | 819512 | 10/1937 |

OTHER PUBLICATIONS

US Patent and Trademark Office, U.S. Appl. No. 10/684,344, filed Oct. 10, 2003, Johnsen et al.
US Patent and Trademark Office, U.S. Appl. No. 29/357,819, filed Mar. 17, 2010, Oien et al.
US Patent and Trademark Office, U.S. Appl. No. 61/529,655, filed Aug. 31, 2011, Oien et al.

(Continued)

*Primary Examiner* — Matthew Nelson
(74) *Attorney, Agent, or Firm* — Kolisch Hartwell, P.C.

(57) ABSTRACT

Dental instrument servicing systems and cushions are disclosed. The dental instrument servicing systems may include a holder and a cushion. The holder may include a passage extending from a first opening to a second opening. The cushion may include first and second portions, with the first portion being configured for selective receipt within the passage and with the second portion extending from the first portion.

12 Claims, 3 Drawing Sheets

(56) References Cited

U.S. PATENT DOCUMENTS

| | | | |
|---|---|---|---|
| 2,488,492 A | 11/1949 | Dumbleton | |
| 2,539,940 A | 1/1951 | Abramson | |
| 2,637,148 A | 5/1953 | Tingvatne | |
| 2,645,013 A | 7/1953 | Mathison | |
| 2,665,479 A | 1/1954 | Weldon | |
| 2,681,772 A | 6/1954 | Charney | |
| 2,929,541 A | 3/1960 | Castelli et al. | |
| 2,942,764 A | 6/1960 | Castelli | |
| 2,967,651 A | 1/1961 | Zackhein et al. | |
| 2,971,637 A | 2/1961 | Simons | |
| 3,016,639 A | 1/1962 | Kennedy et al. | |
| 3,071,299 A | 1/1963 | Brown | |
| 3,072,244 A | 1/1963 | Smith | |
| 3,092,443 A | 6/1963 | Dietz | |
| 3,107,832 A | 10/1963 | Kotkins | |
| 3,136,462 A | 6/1964 | Knutson | |
| 3,246,815 A | 4/1966 | Aronson | |
| 3,265,264 A | 8/1966 | Stephens | |
| 3,275,329 A | 9/1966 | Lieberman et al. | |
| 3,327,391 A | 6/1967 | Malm | |
| 3,331,868 A | 7/1967 | Holden et al. | |
| 3,421,679 A | 1/1969 | Goldman | |
| 3,473,991 A | 10/1969 | Ludwig | |
| 3,503,397 A | 3/1970 | Fogarty et al. | |
| 3,530,979 A | 9/1970 | Merrill, Jr. et al. | |
| 3,579,306 A | 5/1971 | Crane | |
| 3,696,916 A | 10/1972 | Penniman et al. | |
| 3,777,882 A | 12/1973 | McIntyre | |
| 3,881,868 A | 5/1975 | Duke | |
| 3,933,286 A | 1/1976 | Karkas | |
| 3,949,568 A | 4/1976 | Gallagher | |
| 4,026,063 A | 5/1977 | Allen et al. | |
| 4,027,410 A | 6/1977 | Wheeler | |
| 4,079,530 A | 3/1978 | Atherton et al. | |
| 4,136,773 A | 1/1979 | Booth | |
| 4,191,291 A | 3/1980 | Brown | |
| D256,999 S | 9/1980 | Haagedoorn et al. | |
| 4,232,784 A | 11/1980 | Hesselgren | |
| 4,251,482 A | 2/1981 | Sanderson et al. | |
| 4,253,830 A | 3/1981 | Kazen et al. | |
| 4,280,808 A * | 7/1981 | Johnsen et al. | 433/77 |
| 4,306,862 A | 12/1981 | Knox | |
| 4,349,632 A | 9/1982 | Lyman et al. | |
| 4,375,863 A | 3/1983 | Kappler | |
| 4,397,395 A | 8/1983 | McKelvey | |
| 4,402,407 A | 9/1983 | Maly | |
| 4,411,040 A | 10/1983 | Sharrow et al. | |
| 4,427,130 A | 1/1984 | Szigeti | |
| 4,502,485 A | 3/1985 | Burgin | |
| 4,503,972 A | 3/1985 | Nelligan et al. | |
| 4,506,404 A | 3/1985 | Clay | |
| 4,512,471 A | 4/1985 | Kaster et al. | |
| 4,609,126 A | 9/1986 | Janda | |
| 4,634,077 A | 1/1987 | Wilson | |
| 4,643,674 A | 2/1987 | Zdarsky | |
| 4,661,326 A | 4/1987 | Schainholz | |
| 4,694,956 A | 9/1987 | Sims | |
| 4,698,210 A | 10/1987 | Solazzi | |
| 4,706,839 A | 11/1987 | Spence | |
| 4,717,057 A | 1/1988 | Porteous | |
| 4,726,470 A | 2/1988 | Lieberman | |
| 4,762,247 A | 8/1988 | Temmesfeld | |
| 4,772,201 A | 9/1988 | Johnsen et al. | |
| 4,822,280 A | 4/1989 | Rider | |
| 4,844,308 A | 7/1989 | Porteous | |
| 4,859,423 A | 8/1989 | Perlman | |
| 4,867,305 A | 9/1989 | Schneider | |
| 4,888,487 A | 12/1989 | Ritter | |
| 4,901,847 A | 2/1990 | Kesling | |
| 4,925,073 A | 5/1990 | Tarrson et al. | |
| 4,960,220 A | 10/1990 | Foa | |
| 4,973,847 A | 11/1990 | Lackey et al. | |
| 4,976,615 A * | 12/1990 | Kravitz | 433/75 |
| 4,991,759 A | 2/1991 | Scharf | |
| 5,006,066 A | 4/1991 | Rouse | |
| 5,016,795 A | 5/1991 | Porteous | |
| 5,029,252 A | 7/1991 | Ameseder | |
| 5,054,674 A | 10/1991 | Fortman | |
| 5,076,437 A | 12/1991 | Schindler | |
| 5,106,297 A | 4/1992 | Discko, Jr. | |
| 5,108,287 A | 4/1992 | Yee et al. | |
| 5,139,188 A | 8/1992 | Scharf | |
| 5,154,611 A | 10/1992 | Calvin | |
| 5,156,290 A | 10/1992 | Rodrigues | |
| 5,160,077 A | 11/1992 | Sticklin | |
| 5,172,810 A | 12/1992 | Brewer | |
| 5,219,525 A | 6/1993 | Harrison | |
| 5,246,105 A | 9/1993 | Eykmann et al. | |
| 5,249,963 A | 10/1993 | McGarrigle | |
| D341,909 S | 11/1993 | Schneider | |
| 5,282,563 A | 2/1994 | Oliver et al. | |
| 5,340,550 A | 8/1994 | Johnsen et al. | |
| 5,358,112 A | 10/1994 | Gardner | |
| 5,368,482 A * | 11/1994 | Johnsen et al. | 433/163 |
| 5,369,902 A | 12/1994 | Minster | |
| 5,372,252 A | 12/1994 | Alexander | |
| 5,377,823 A | 1/1995 | Steen et al. | |
| D356,655 S | 3/1995 | Maniago | |
| 5,456,361 A | 10/1995 | Walsh et al. | |
| D366,537 S | 1/1996 | Johnsen et al. | |
| 5,525,314 A | 6/1996 | Hurson | |
| 5,538,421 A | 7/1996 | Aspel | |
| 5,629,527 A | 5/1997 | Levitt et al. | |
| 5,645,206 A | 7/1997 | Ippisch | |
| 5,716,584 A | 2/1998 | Baker et al. | |
| 5,749,730 A | 5/1998 | Johnsen et al. | |
| RE36,072 E | 2/1999 | Uy | |
| 5,913,422 A | 6/1999 | Cote et al. | |
| 5,967,778 A * | 10/1999 | Riitano | 433/77 |
| 5,989,699 A | 11/1999 | Kuczynski et al. | |
| 6,036,490 A * | 3/2000 | Johnsen et al. | 433/102 |
| 6,257,888 B1 | 7/2001 | Barham | |
| 6,322,363 B1 | 11/2001 | Beecher et al. | |
| 6,325,968 B1 | 12/2001 | Fricker et al. | |
| 6,436,351 B1 | 8/2002 | Gubernator et al. | |
| 6,464,497 B2 | 10/2002 | Landoz | |
| 6,485,822 B1 | 11/2002 | Osiecki et al. | |
| 6,564,490 B1 | 5/2003 | Avila | |
| 6,681,925 B2 | 1/2004 | Fischer et al. | |
| 6,685,376 B2 | 2/2004 | Weihrauch | |
| 6,687,925 B2 | 2/2004 | Minnick | |
| 6,719,560 B2 | 4/2004 | Capt | |
| 6,722,067 B1 | 4/2004 | Kennedy et al. | |
| 6,742,659 B2 | 6/2004 | Clark et al. | |
| 6,776,616 B2 | 8/2004 | Dryer | |
| 6,890,115 B2 * | 5/2005 | Le Moing, II | 401/82 |
| 7,763,038 B2 * | 7/2010 | O'Brien | 606/148 |
| 8,231,734 B2 | 7/2012 | Johnsen et al. | |
| D689,190 S | 9/2013 | Oien et al. | |
| 2001/0035384 A1 | 11/2001 | Davis et al. | |
| 2003/0039942 A1* | 2/2003 | Phillips | 433/140 |
| 2004/0068820 A1* | 4/2004 | Johnsen et al. | 15/244.1 |
| 2004/0139642 A1* | 7/2004 | Johnsen et al. | 40/661.11 |
| 2006/0019217 A1 | 1/2006 | Yates | |
| 2006/0166170 A1* | 7/2006 | Masters | 433/215 |
| 2006/0270747 A1 | 11/2006 | Griggs | |
| 2007/0205124 A1 | 9/2007 | Johnsen et al. | |
| 2008/0311543 A1* | 12/2008 | Viscomi et al. | 433/163 |
| 2009/0136896 A1 | 5/2009 | Meyer Shuster | |
| 2011/0068031 A1 | 3/2011 | Johnsen et al. | |

OTHER PUBLICATIONS

Dec. 24, 2012, International Search Report from The U.S. Receiving Office in PCT/US2012/53529, which is the another application of Inventors Oien and Johnsen.

Dec. 24, 2012, Written Opinion of the International Searching Authority from The U S. Receiving Office in PCT/US2012/53529, which is another application of Inventors Oien and Johnsen.

* cited by examiner

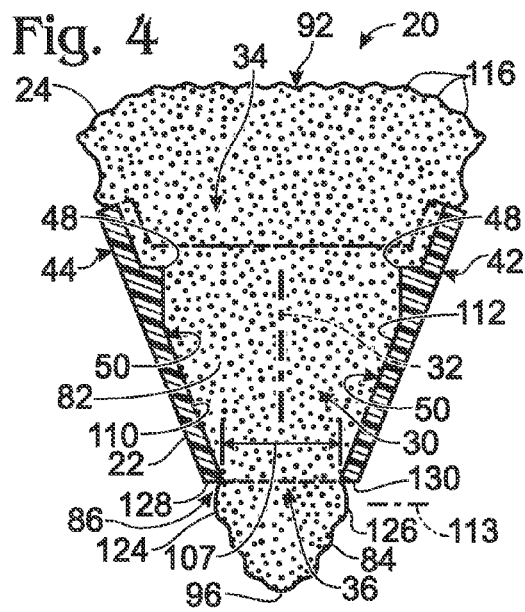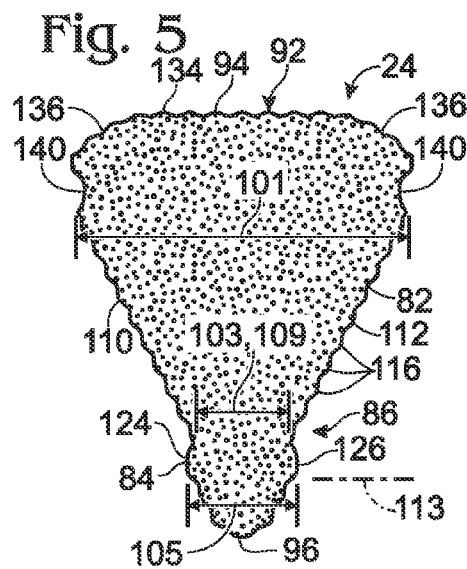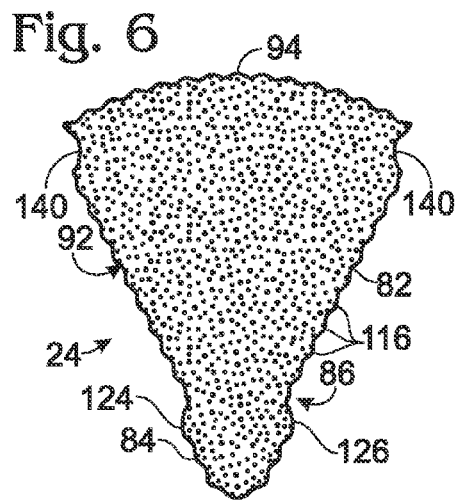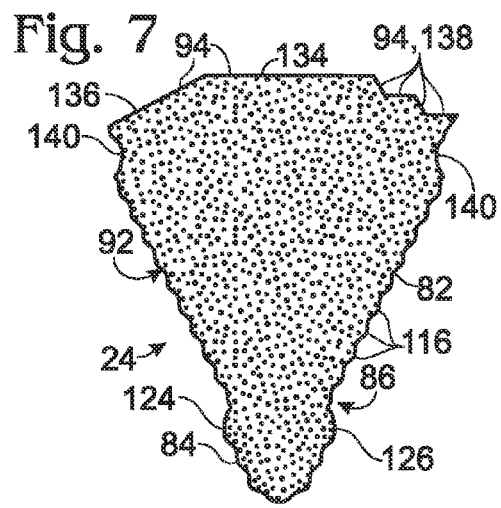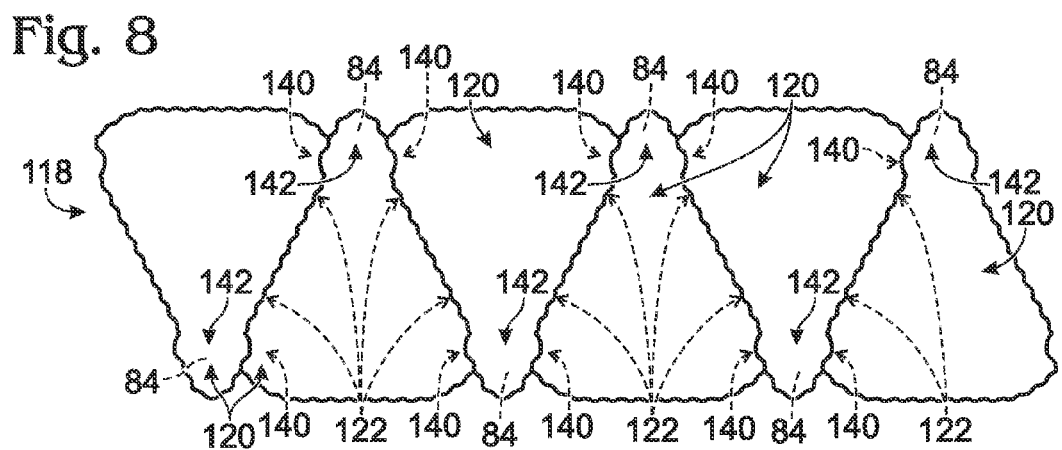

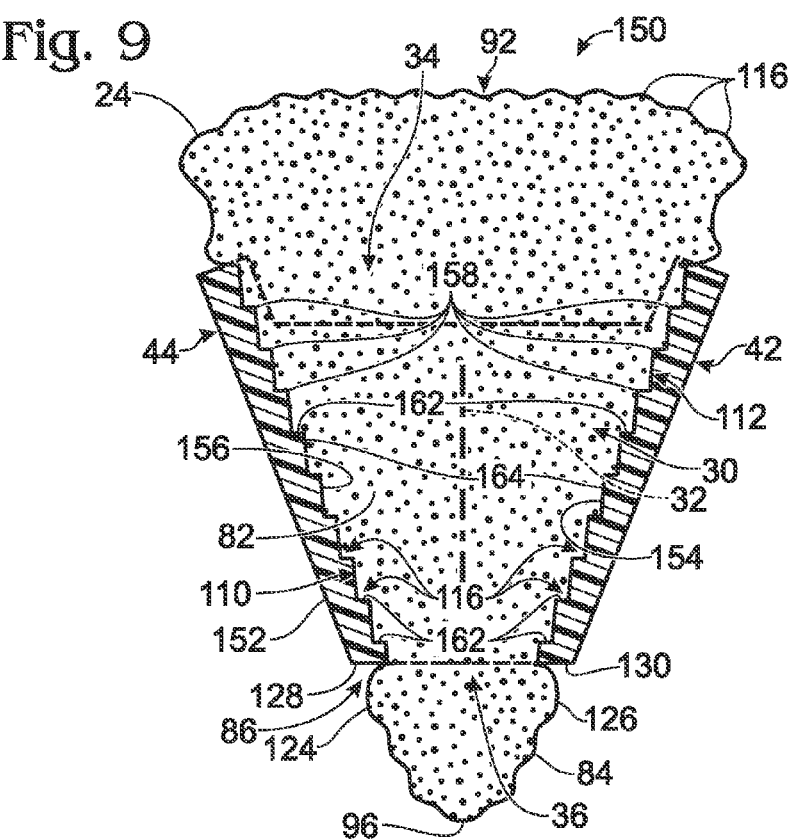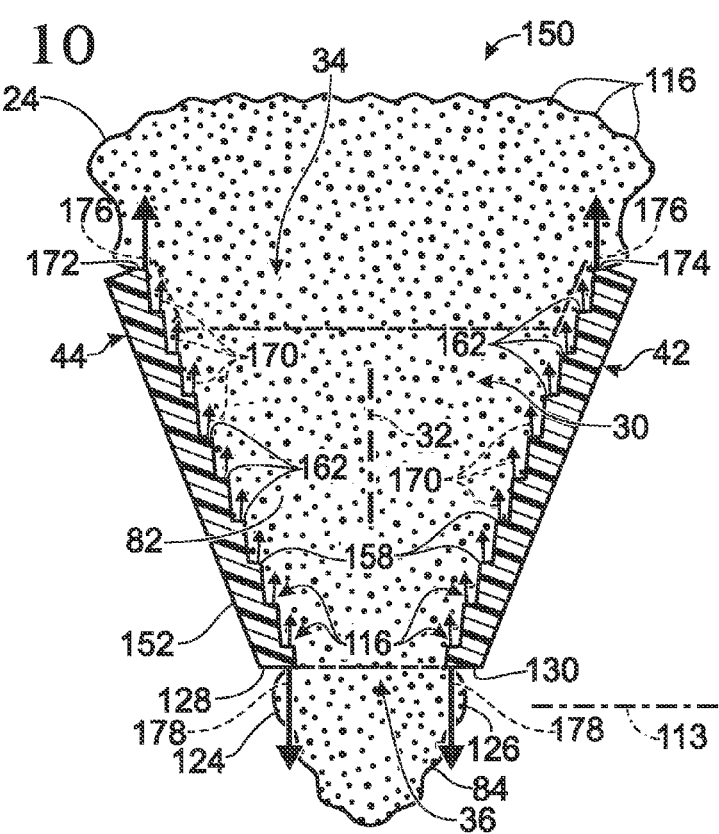

DENTAL INSTRUMENT SERVICING SYSTEM

BACKGROUND

Dental instrument servicing systems may be used to receive and retain, temporarily store and/or clean various dental instruments such as during a dental procedure. For example, a dentist may use a dental instrument servicing system to receive and retain, temporarily store and/or clean endodontic files during an endodontic procedure. Such dental instrument servicing systems may employ foam cushion inserts for use in servicing endodontic files. Examples of dental instrument servicing systems with foam cushion inserts are disclosed in U.S. Pat. Nos. 4,280,808; 4,976,615; 5,368,482 and 6,036,490; and in U.S. Patent Application Publication Nos. US 2004/0068820 A1; US 2004/0139642 A1 and US 2007/0205124 A1. The disclosures of these and all other publications referenced herein are incorporated by reference in their entirety for all purposes.

BRIEF DESCRIPTION OF THE DRAWINGS

FIG. 4 is a section view of the dental instrument servicing system of FIG. 1, taken generally along line 4-4 in FIG. 3.

FIG. 5 is a front view of the foam cushion insert employed in the dental instrument servicing system in FIGS. 1-4, the foam cushion insert having been removed from the holder.

FIG. 6 is a front view of another nonexclusive illustrative example of a foam cushion insert suitable for use in connection with the dental instrument servicing system of FIG. 1.

FIG. 7 is a front view of another nonexclusive illustrative example of a foam cushion insert suitable for use with the dental instrument servicing system of FIG. 1.

FIG. 8 shows a nonexclusive illustrative example of a cutting pattern for a die for cutting out multiple copies of the foam cushion insert of FIG. 5.

FIG. 9 is a section view of another nonexclusive illustrative example of a dental instrument servicing system, taken generally along a line corresponding to the line 4-4 in FIG. 3.

FIG. 10 is a section view similar to FIG. 9 of the dental instrument servicing system of FIG. 9, showing various force vectors.

DETAILED DESCRIPTION OF THE DISCLOSURE

Figure 1:
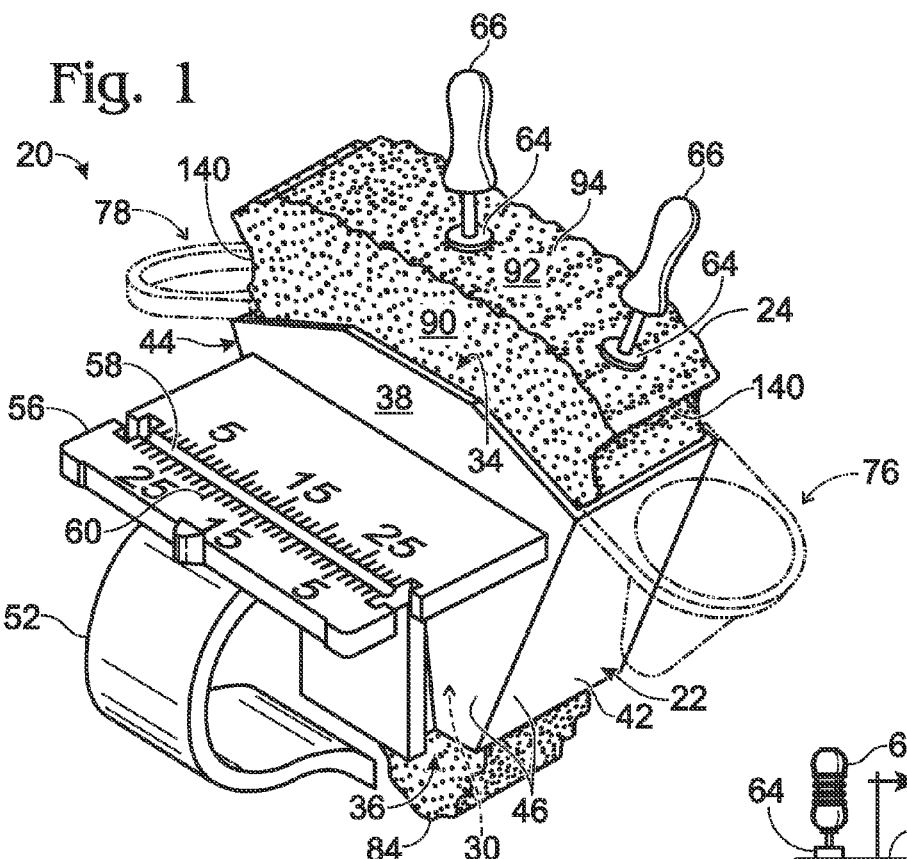
FIG. 1 is a perspective view of a nonexclusive illustrative example of a dental instrument servicing system that includes a nonexclusive illustrative example of a foam cushion insert.

A nonexclusive illustrative example of a dental instrument servicing system is shown generally at 20 in FIG. 1. The dental instrument servicing system 20 includes a holder 22 and a foam cushion insert or cushion 24. Unless otherwise specified, the dental instrument servicing system 20 and/or the cushion 24, may contain at least one of the structures, components, functionalities, and/or variations described, illustrated, and/or incorporated herein.

Figure 2:
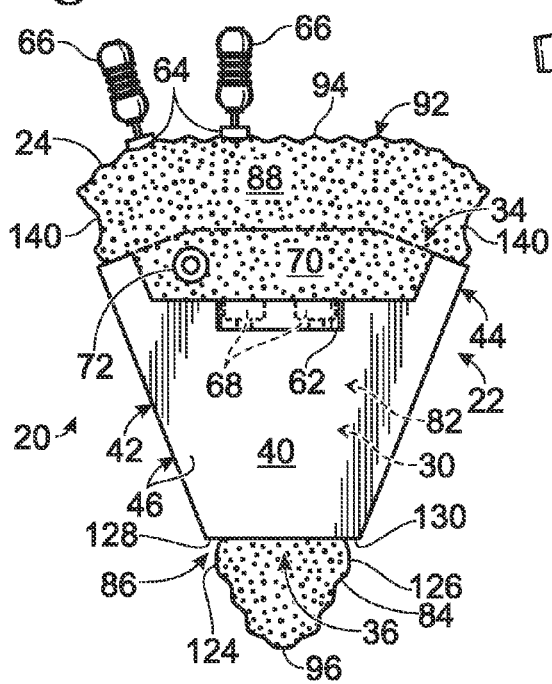
FIG. 2 is a rear view of the dental instrument servicing system of FIG. 1.
Figure 3:
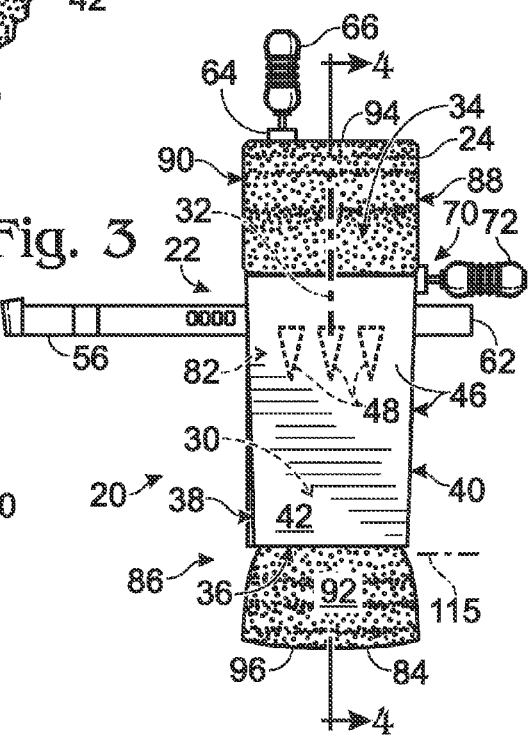
FIG. 3 is a side view of the dental instrument servicing system of FIG. 1, with the finger mount shown removed.

The holder 22, which may be formed from molded plastic, may include one or more walls that together define a passage 30 that extends at least partially through the holder 22 along an axis 32 and from a first opening 34 to a second opening 36. For example, as shown in FIGS. 1-3, the holder 22 may include opposed front and back walls 38, 40 and opposed side walls 42, 44. The passage 30 may extend substantially completely through the holder 22 with the first and second openings 34, 36 being disposed on an exterior surface 46 of the holder 22, as shown in FIGS. 1-4, or the passage may be blind, such as where the second opening 36 connects the passage 30 to a cavity within the holder.

As will be more fully discussed below, the holder 22 may be configured to releasably receive the cushion 24 with at least a portion of the cushion extending through the passage 30. As the cushion may be somewhat abrasive and/or have a relatively rough surface, the cushion 24 may be at least partially frictionally retained within the passage 30. In some examples, the frictional engagement between the cushion 24 and the walls of the passage 30 may be enhanced by the provision of one or more projections 48 disposed on the interior surface 50 of one of more of the walls of the holder 22. As shown and suggested in FIGS. 3 and 4, the projections 48 may be substantially pyramidal in shape.

The shape and/or geometry of the passage 30 may be selected to receive a cushion 24 having a particular shape. For example, when intended for use with a generally wedge-shaped cushion 24, the walls of the passage 30 may generally converge. Thus, as shown in FIGS. 1-4, passage 30 may generally be configured as a frustum of a pyramid with the first opening 34 having a first cross-sectional area and the second opening 36 having a second cross-sectional area smaller than the first cross-sectional area. For example, the front and back walls 38, 40 may converge at a first suitable angle, such as about zero to about five degrees, while the side walls 42, 44 may converge at a second suitable angle, such as about 40 to about 60 degrees. However, in some examples, the side walls may converge while the front and back walls may be substantially parallel. In holders 22 where the convergence angle of the side walls 42, 44 is larger than the convergence angle of the front and back walls 38, 40, as shown in FIGS. 1-4, the first and second openings 34, 36 have different shapes, with the first opening 34 being generally rectangular and the second opening 36 being generally square. However, in some examples, the first and second openings 34, 36 may have similar shapes, such as where both openings are generally square. In some examples, rather than having converging walls, the passage 30 may have an at least partially cylindrical or constant cross-section, with the cross-section being circular, ellipsoidal, polygonal, or even square.

In some examples, the dental instrument servicing system 20 may be configured to be worn and/or supported on a user's hand. For example, as shown in FIG. 1, a finger band or mount 52 may be attached to the holder 22, with the finger mount being configured to position and/or support the dental instrument servicing system 20 on a user's finger, such as the user's forefinger, for use during a dental procedure. The finger mount 52 may be removably attached to the holder 22 by way of a latching slide arrangement, such as that described in U.S. Pat. No. 4,280,808, the disclosure of which has been incorporated by reference above. A variety of different-sized finger mounts may be provided and/or used with the dental instrument servicing system 20.

As shown in FIG. 1, some examples of the holder 22 may include an outwardly projecting shelf 56. The shelf may extend outward, covering the finger mount 52, and may protect a user's finger from injury by sharp instruments, such as endodontic files, which may be inserted into the cushion 24. The shelf 56 may further serve as a measuring device for use in connection with endodontic files. Thus, the shelf 56 may include a trough 58 for receipt of endodontic files. A scale 60 may be molded and/or etched into shelf 56, which may permit accurate positioning of depth markers on an endodontic file. The use of such a measuring device is more fully described in the aforementioned U.S. Pat. No. 4,280,808, the disclosure of which has been incorporated by reference above.

As shown in FIGS. 2 and 3, some examples of the holder 22 may include a service platform 62, which may project from the back wall 40. The service platform may be adapted to receive depth markers 64, such as those shown on the endodontic files 66. As shown, the service platform 42 may include one or more recessed openings 68, each of which may be configured to hold one or more depth markers 64.

In some examples, the back wall 40 of the holder 22 may be lowered relative to the front wall 38 to provide for an enlarged docking area 70 for endodontic files, as shown in FIG. 2. The docking area may provide an increased area to place files and/or other instruments. Thus, an instrument, such as the endodontic file 72 shown in FIGS. 2 and 3, may be inserted substantially perpendicularly to the files 66. Such a docking area may enable, a dental assistant to perform a safe pick up without causing the doctor to break his/her visual field while operating under a surgical microscope. Moreover, the presence of the taller front wall 38 may operate as a safety shield. Thus, front wall 38 may shield the dental instrument servicing system wearer, such as the dental assistant, from endodontic files that are inserted into the docking area 70 of cushion 24.

The holder 22 may be configured to accommodate a medicament in a readily accessible position. For example, as shown in FIG. 1, a medicament cup 76 and/or cup-holder ring 78 configured to receive and retain a dosage container may be removably attached to the holder 22. The medicament cup 76 and the cup-holder ring 78 may include clip sections (not shown) configured to selectively attach the medicament cup 76 and/or the cup-holder ring 78 to the holder 22, such as to one of the side walls 42, 44. The attachment of the medicament cup 76 and the cup-holder ring 78 to the holder 22 is more fully described in the aforementioned U.S. Pat. No. 6,036,490, the disclosure of which has been incorporated by reference above.

The cushion 24, which is configured to receive and releasably hold plural endodontic files, such as files 66, 72, may comprise and/or be fabricated from a foam material. In some examples, the cushion may be fabricated from an open-cell foam material such as a urethane foam having a density of about 20-30 kg per cubic meter; a cell count of about 15-16 cells per centimeter; an air flow of about 1.0-4.5 cubic decimeters per second (as measured according to standard ASTM D 3574 Air Flow Test G); a 25% indentation force deflection (IFD—as measured according to standard ASTM D 3574 Test B) of about 80 to 120 newtons; and a 50% compression force deflection (CFD—determined from the force required to compress an entire sample surface area to 50% of its sample height) of about 2.5-3.0 newtons. The foam characteristics may be balanced to achieve a suitable material for releasably receiving and holding instruments and/or for use in insertion cleaning. Selection of one or more of the density, material, and cell count of the foam may effect a change in the air flow, the IFD, the CFD, or other characteristic of the cushion. For example, selection of the appropriate material may include balancing the density and cell count of the foam, such that the foam functions as desired.

As shown in FIGS. 1-5, the cushion 24 may include a first or main portion or body 82, a second portion or enlarged tip 84 extending from the body 82, a neck region 86 between the body 82 and the enlarged tip 84, first and second spaced-apart surfaces 88, 90, and a peripheral or edge surface 92 extending between the first and second surfaces 88, 90. The cushion 24 may extend from a working portion 94 of the peripheral surface 92, which may be proximate the main portion or body 82, to the distal end 96 of the cushion 24, which may be proximate the second portion or enlarged tip 84. The peripheral surface 92 may at least partially circumscribe at least one of the first and second surfaces 88, 90 and may be substantially perpendicular to at least one of the first and second surfaces.

The cushion 24 may be configured to be releasably received by the holder 22, as shown in FIGS. 1-4, with the body 82 of the cushion received within and extending through the passage 30, the enlarged tip 84 extending beyond the second opening 36, and the neck region 86 proximate the second opening 36. For example, where the cushion 24 is substantially uncompressed, such as when the cushion is not received by the holder 22 as shown in FIG. 5, the body 82 may taper from a first lateral dimension or width 101 proximate the working portion 94 of the peripheral surface to a second lateral dimension or width 103 proximate the enlarged tip 84, with the second width 103 being less than the first width 101.

At least a part of the enlarged tip 84 may have a third lateral dimension or width 105 that is greater than the second width 103. As shown in FIG. 5, the third width 105 may be a maximum width of the enlarged tip 84 and may be less than the first width 101. In some examples, the third width 105 may be at least 115% as great as the second width 103. As shown in FIG. 4, the third width 105 of the enlarged tip 84 may be larger than a fourth lateral dimension or width 107 of the second opening 36 when the enlarged tip 84 is substantially uncompressed. As shown in FIG. 5, the neck region 86 may have a fifth lateral dimension or width 109, which may correspond to the second width 103 of the body 82, with the fifth width 109 being smaller than the third width 105 of at least a part of the enlarged tip 84, such as when the enlarged tip 84 and the neck region 86 are substantially uncompressed. In some examples, the fifth width 109 may be no larger than approximately the fourth width 107 of the second opening 36 when the neck region 86 is substantially uncompressed.

As used herein, the first, second, third, fourth and fifth lateral dimensions or widths 101, 103, 105, 107 and 109 may be measured as is generally shown in FIGS. 4 and 5. In particular, the first, second, third and fifth lateral dimensions or widths may be measured between first and second opposed portions 110, 112 of the peripheral surface 92 in directions or along axes that may be substantially parallel to at least one of the first and second surfaces 88, 90 and may be substantially transverse to the axis 32 of the passage 30 when the cushion 24 is releasably received by the holder 22. The fourth lateral dimension or width may be measured between opposed first and second edge sections 128, 130 of the second opening 36 in a direction or along an axis that may be substantially parallel to the axis along which at least one of the first, second, third and fifth lateral dimensions or widths is measured. By "transverse" or "transversely," it is meant that the indicated elements are obliquely or perpendicularly oriented.

By way of a non-limiting example with regard to the holder 22 and cushion 24 illustrated in FIGS. 1-5, the fourth width 107 of the second opening 36 may be about, or slightly more than, 0.5 inches (12.7 mm), with the second width 103 of the body 24 and the fifth width 109 of the neck region 86 being approximately 0.5 inches (12.7 mm). The parts of the first and second opposed portions 110, 112 of the peripheral surface 92 that correspond to the body 82 of the cushion 24, namely the lateral edges of the body 82 of the cushion 24, may diverge from the neck region 109 at a suitable angle, such as about 35 to about 65 degrees. The divergence angle of the lateral edges of the body 82 of the cushion 24 may be less than, approximately equal to, or even greater than the convergence angle of the side walls 42, 44 of the passage 30. For example, the lateral edges of the body 82 of the cushion 24 shown in FIGS. 4 and 5 diverge from the neck region 109 at an angle that is approximately equal to the convergence angle of the side walls 42, 44 of the holder 22 shown in FIGS. 1-4.

A greater divergence angle of the lateral edges of the body of the cushion 24 relative to the convergence angle of the side walls of the passage 30 may enhance the frictional engagement of the cushion within the passage such as by permitting the cushion to be wedged into the passage. Thus, when the cushion 24 is releasably received by the holder 22 with the neck region 86 proximate the second opening 36, as shown in FIG. 4, a portion of the body 82 that is spaced away from the neck region 86 may be compressed in at least a first or lateral direction or dimension, such as in a direction or dimension corresponding to or along axis 113, that generally corresponds to the fifth width 109. However, the neck region 86 and the enlarged tip 84 may remain substantially uncompressed in at least the lateral dimension corresponding to the axis 113 because the fourth width 107 of the second opening 36 may be at least as great as the second and fifth widths 103, 109 of the cushion 24. In some examples, the neck region 86 and the enlarged tip 84 may remain substantially uncompressed in all dimensions.

However, even though the neck region 86 may remain substantially uncompressed in the lateral dimension corresponding to the axis 113, in some examples, the neck region 86 may be compressed in a second direction or transverse dimension, such as in a direction or dimension corresponding to or along axis 115, that is transverse to insertion axis 32 and transverse to the axis 113 when the cushion 24 is releasably received by the holder 22 with the neck region 86 proximate the second opening 36, as shown in FIGS. 3 and 4. In particular, the thickness of the cushion 24 may be greater than the dimension of the second opening 36 that corresponds to the axis 115 such that at least a portion of the neck region 86 may be compressed in the dimension corresponding to the axis 115 while the enlarged tip 84 of the cushion bulges outward relative to the second opening 36, as shown in FIG. 3. By way of a non-limiting example with regard to the holder 22 and cushion 24 illustrated in FIGS. 1-5, the thickness of the foam material used for the cushion 24 may be about 0.7-0.8 inches (17.8-20.3 mm) while the corresponding dimension of the second opening 36 may be about 0.5 inches (12.7 mm).

In examples where the divergence angle of the lateral edges of the body 82 of the cushion 24 is approximately equal to the convergence angle of the side walls 42, 44 of the passage 30, the cushion 24 may be substantially uniformly compressed, or even substantially uncompressed, when the cushion is releasably received by the holder 22. In such an example, at least the body 82 of the cushion 24 may be substantially uncompressed in at least a lateral direction or dimension, such as a direction or dimension corresponding to axis 113, when the cushion 24 is releasably received in the passage 30 with the neck region 86 proximate the second opening 36. When the body of the cushion is substantially uniformly compressed or substantially uncompressed, the density of the cushion may be substantially uniform which may allow substantially uniform and/or consistent insertion and/or retention forces exerted on instruments, such as the endodontic files 66, 72 shown in FIGS. 1-3, that may be independent of the insertion depth and/or the insertion location of the instrument.

The presence of an enlarged tip 84 on the cushion 24 that is relatively wider than the neck region 86 and/or the second opening 36 on the holder 22 may provide a visual indication that the cushion is properly received by the holder. For example, when the cushion 24 is inserted through the first opening 34 and subsequently pulled through the second opening 36, the complete emergence of the enlarged tip 84 beyond the second opening 36, and/or partial exposure of the neck region 86 at the second opening, may indicate that the body 82 of the cushion is properly and/or fully received within the passage 30. A user may use the indication that the cushion is properly and/or fully received within the passage to fully and/or consistently insert cushions 24 into the holder 22. Consistent proper and/or full insertion of the cushion may result in the cushion being substantially uncompressed or being predictably, consistently and/or uniformly compressed, in at least a lateral direction or dimension corresponding to axis 113, which may result in the cushion providing consistent retention forces and/or cleaning of the instruments that are used with the dental instrument servicing system 20. For example, proper insertion of the cushion may prevent unintended compression of the cushion that may result from the cushion being wedged between the converging side walls 42, 44 of the passage 30. In some examples, proper insertion may result in predictable and consistent compression of the cushion when the cushion is properly wedged between the converging side walls.

In addition to providing for consistent compression or preventing unintended compression of the cushion in at least a lateral direction or dimension corresponding to axis 113, proper or consistent insertion of the cushion may also provide for consistent compression or prevent unintended compression of the cushion in a direction or dimension corresponding to axis 115. However, a smaller convergence angle between the front and back walls 38, 40 relative to the convergence angle between the side walls 42, 44 may result in relatively less unintended compression and/or variation in compression in a direction or dimension corresponding to axis 115 than in a lateral direction or dimension corresponding to axis 113, such as at least proximate the first opening 34.

In addition, the enlarged tip 84, being relatively wider than the second opening 36, as generally discussed above, may tend to impede inadvertent removal of the cushion 24 from the holder 22. In some examples, the enlarged tip 84 may provide for or enhance retention of the cushion 24 within the passage 30 of the holder 22.

Furthermore, the enlarged tip 84, being relatively bulkier than the sharply pointed cushions described in U.S. Pat. No. 4,280,808, the disclosure of which has been incorporated by reference above, may result in the cushion 24 being more readily pulled through the second opening 36 during installation. For example, the cushion 24 and/or its enlarged tip 84 may be more readily gripped by a user, and/or be more resistant to tearing, when pulled through the second opening 36.

As shown in FIGS. 1-5, the peripheral surface 92 may include a plurality of ridges or corrugations 116 extending transversely to the first and second surfaces 88, 90. In some examples, at least some of the plurality of ridges or corrugations 116 may extend substantially perpendicularly to at least one of the first and second surfaces 88, 90. For example, the cushion 24 may have a constant thickness such that, prior to the body 82 of the cushion 24 being received within the passage 30, the first and second surfaces 88, 90 may be parallel and the corrugations 116 may extend substantially perpendicularly to the first and second surfaces 88, 90. The ridges or corrugations 116 may be rounded, as shown in FIGS. 1-5, or they may include a plurality of angularly intersecting flat surfaces that may provide a stepped or sawtooth configuration.

The ridges or corrugations may enhance the retention of the cushion 24 within the passage 30 of the holder. For example, the corrugations may increase and/or enhance the frictional engagement between the peripheral surface 92 of the cushion and the interior surfaces 50 of the side walls 42, 44 and/or the projections 48. In examples where the cushions are die-cut from a sheet of foam material, the wavy or undulating die used to cut the corrugations may result in a stronger and/or more durable cutting die.

In some examples, the presence of corrugations on the peripheral surface 92 of the cushions 24 may conceal manufacturing and/or packaging artifacts or features that might be present on the peripheral surfaces of the cushions. For example, multiple cushions may be manufactured and/or supplied as a multiple-unit array comprising a plurality of cushions that were cut using a single die, such as the die 118 shown in FIG. 8, and which cushions may remain at least partially connected after being cut by the die. The die 118 may include a plurality of openings 120 configured to cut the plurality of cushions. In some examples, the die 118 may include portions, as generally indicated at 122, that are configured to not cut, or less than fully cut, the material being used to fabricate the cushions such that the cushions in the multiple-unit array may remain at least partially connected by the bridges of material left uncut due to the portions 122 of the die 118. In such examples, the presence of the corrugations on the peripheral surfaces of the separated individual cushions may conceal the remnants of the bridges of uncut material that had connected the plurality of individual cushions into a multiple-unit array, which may improve the appearance of the cushions.

When multiple cushions are cut using a single die, the die may be configured to arrange the cushions in a manner that accommodates cooperative packaging of the cushions and/or efficiently uses the material from which the cushions are cut. For example, the die 118 shown in FIG. 8 includes six openings 120 arranged to cut six cushions relatively efficiently, such as from a relatively small piece of material, which may minimize waste and arrange the resulting multiple-unit array of six cushions relatively compactly to allow for efficient cooperative packaging of the cut, but still connected, array of cushions.

The peripheral surface 92 may include first and second ridges 124, 126 disposed on opposed portions of the peripheral surface 92. As shown in FIG. 5, the first and second ridges 124, 126, which may be relatively larger and/or more prominent than the ones of the plurality of corrugations 116 proximate the ridges, may provide a transition between the body 82 and the enlarged tip 84 of the cushion 24. In addition, as suggested by FIG. 5, a cross-section of the enlarged tip 84 proximate or through the first and second ridges 124, 126 may be wider and/or larger in a lateral direction or dimension corresponding to or along at least the first axis 113 than a cross-section of the body 82 proximate the neck region 86. In some examples, the cross-section of the enlarged tip 84 proximate the first and second ridges 124, 126 may be wider and/or larger than the cross-sectional area of the second opening 36. A wider and/or larger cross-section of the enlarged tip 84 relative to the cross-sectional area of the second opening 36 may impede removal of the cushion 24 from the passage 30. In some examples, a wider and/or larger cross-section of the enlarged tip 84 relative to the cross-sectional area of the second opening 36 may provide for or enhance retention of the cushion 24 within the passage 30 of the holder 22.

As shown in FIGS. 2 and 4, the first and second ridges 124, 126 may engage respective first and second opposed edge sections 128, 130 of the second opening 36 when the body 82 of the cushion 24 is received within the passage 30 with the enlarged tip 84 of the cushion 24 extending beyond the second opening 36. The engagement of the first and second ridges 124, 126 with the first and second edge sections 128, 130 may at least partially impede removal of the cushion 24 from the passage 30, provide for or enhance retention of the cushion 24 within the passage 30, and/or provide an indication that the body 82 of the cushion 24 is fully and/or properly received within the passage 30.

As shown in FIGS. 5-7, cushions 24 may be fabricated with variously configured peripheral surface working portions 94. For example, as shown in FIG. 5, the working portion 94 of the peripheral surface 92 may include a generally planar or flat central portion 134 and a pair of lateral portions 136, any combination of which may be smooth or corrugated. The lateral portions 136 may be curved, as shown in FIG. 5, or they may be substantially flat. As shown in the example of FIG. 6, the working portion 94 of the peripheral surface 92 may include a single curved surface, which may be smooth and/or corrugated, and may have a fixed or variable radius of curvature. As shown in the example of FIG. 7, the working portion 94 of the peripheral surface 92 may include a substantially flat central portion 134, an angled peripheral portion 136, and a stepped peripheral portion 138. Although the illustrative examples of cushions presented in FIGS. 1-7 include particular combinations of corrugated and smooth portions of the peripheral surface 92, it should be understood that the cushions 24 may include any combination of corrugated and/or smooth portions of the peripheral surface 92. For example, the working portions 94, the first and second opposed portions 110, 112, and/or the enlarged tip 84 may include any combination of corrugated portions, as with portions 134 and 136 in FIG. 5, and/or substantially smooth portions, as with portions 134, 136 and 138 in FIG. 7.

Furthermore, when multiple examples of the cushions shown in FIGS. 5-7 are cut using a single die such as that shown in FIG. 8, the arrangement of the openings 120 on the die 118 may result in the cushions 24 including a pair of notches or cutouts 140 proximate the working portion 94 of the peripheral surface 92. These cutouts may result from, and correspond to, the portions 142 of the openings 120 that cut the enlarged tip 84 and/or the first or second ridges on adjacent ones of the cushions cut by the die. As may be seen in FIGS. 1 and 2, the cutouts 140 may provide a visual indication that the body 82 of the cushion 24 is fully and/or properly received within the passage 30.

Another nonexclusive illustrative example of a dental instrument servicing system is shown generally at 150 in FIG. 9. The dental instrument servicing system 150 includes a holder 152 and a foam cushion insert or cushion 24. Unless otherwise specified, the dental instrument servicing system 150 and/or the holder 152, may contain at least one of the structures, components, functionalities, and/or variations described, illustrated, and/or incorporated herein.

In some examples, the holder 152 may include features or structures disposed on the interior surface of one of more of the walls of the holder 152 that may assist and/or enhance the engagement and/or retention of the cushion 24 within the passage 30. For example, as shown in FIG. 9, the interior surfaces 154, 156 of the opposed side walls 42, 44, which define at least a portion of the passage 30, may include a plurality of ridges 158 that may extend generally transversely to the axis 32 along which the passage 30 extends. At least some of the ridges 158 may extend substantially the entire width of the interior surfaces 154, 156. However, in some examples, at least some of the ridges 158 may extend less than the entire width of the interior surfaces and/or may be discontinuous along their length. As shown in FIG. 9, the plurality of ridges 158 may be disposed along substantially the entire length of the interior surfaces 154, 156. However, in some examples, at least a portion of the interior surfaces 154, 156 may not include ridges.

In some examples, each of the ridges 158 may be sized and/or shaped to engage a respective one of the corrugations 116 on the lateral edges of the body 82 of the cushion 24. For example, as shown in FIG. 9, each of the ridges 158 may include first and second surfaces 162, 164, each of which may each be substantially flat. The first surfaces 162 may be transverse or even perpendicular to the axis 32. As shown in FIG. 9, the first surfaces 162 may be slightly inwardly sloped relative to the axis 32, which may conform to the corrugations 116. The second surfaces 164 may be generally aligned with the axis 32. As shown in FIG. 9, the second surfaces 164 may be slightly outwardly angled relative to the axis 32 to provide a draft angle on the second surfaces 164 and/or to conform to the corrugations 116. In some examples, the second surfaces 164 may be parallel to the axis 32 or even inwardly angled relative to the axis 32, such that the ridges 158 may even have an undercut configuration.

In some examples, engagement between the ridges 158 and corresponding ones of the corrugations 116, as shown in FIG. 10, may provide an indication when the cushion 24 has been properly and/or fully received within the passage 30 of the holder 152. Such an indication may aid with consistently inserting cushions 24 into the holder 152, which may result in the cushion being predictably, consistently and/or uniformly compressed or even uncompressed. The indication may be in the form of a relatively abrupt or discontinuous increase in the force needed to cause further insertion of the cushion that occurs when the first surfaces 162 of the ridges 158 engage corresponding ones of the corrugations 116. In particular, after the ridges engage corresponding ones of the corrugations, further insertion of the cushion may require a noticeable increase in insertion force as the first surfaces, which may be nearly perpendicular to the axis 32, bear on and laterally compress the cushion. For example, where the divergence angle of the lateral edges of the body 82 of the cushion 24 is approximately equal to the convergence angle of the side walls 42, 44 of the passage 30, proper insertion of the cushion to the point where the first surfaces 162 of the ridges 158 engage corresponding ones of the corrugations 116 may result in the cushion undergoing relatively little compression in a lateral direction or dimension corresponding to axis 113 or even being substantially uncompressed in that lateral direction or dimension. However, further insertion of the cushion may then require a relatively significant lateral compression of the cushion over a relatively short insertion distance as the first surfaces 162 of the ridges 158 act on corresponding ones of the corrugations 116, as suggested by the arrows 170 in FIG. 10, to laterally compress the cushion and resist further insertion.

In some examples, proper insertion of the cushion, with the enlarged tip 84 beyond the second opening 36, may result in the cushion 24 being predictably stabilized in the holder 152 with the cushion in a substantially uncompressed condition. For example, as suggested in FIG. 10, further insertion of the cushion may be resisted or opposed by forces resulting from the opposed edges 172, 174 of the first opening 34 bearing on the cushion 24, as suggested by the arrows 176, and/or by forces resulting from the edges 158 and/or the surfaces 162 bearing on corresponding ones of the corrugations 116, as suggested by the arrows 170. Removal of the cushion may be resisted or opposed by forces resulting from the enlarged tip 84 bearing against the holder 152 proximate the second opening 36. In particular, forces resulting from the first and second ridges 124, 126 and/or the enlarged tip 84 bearing on the first and second opposed edge sections 128, 130 of the second opening 36, as suggested by the arrows 178 in FIG. 10, may resist or oppose removal of the cushion 24 form the holder 152. Accordingly, an equilibrium between the forces resisting or opposing further insertion of the cushion and the forces resisting or opposing removal of the cushion may tend to stabilize the cushion 24 in the holder 152. In some examples, such an equilibrium may occur when the forces resisting or opposing further insertion and the forces resisting or opposing removal are both approximately zero, in which case the cushion may be predictably stabilized within the holder with the cushion in a substantially uncompressed condition.

In some examples, such stabilization of the cushion within the holder may include and/or be enhanced by a slight tensile loading within the cushion 24, such as along the axis 32. Such a tensile loading may be induced by the opposing forces suggested by the arrows 170, 176, 178 in FIG. 10, with the opposing forces being nonzero, but in equilibrium, when the cushion in stabilized. In some examples, such forces may be induced in a properly seated cushion when the body of the cushion is shorter than the passage and/or when the effective or nominal divergence angle of the edges of the body of the cushion is larger than the convergence angle of the side walls of the passage.

The intersections between adjacent ones of the first and second surfaces 162, 164 may be relatively sharp, as shown in FIG. 9. However, in some examples the first and second surfaces 162, 164 may be curved and/or the intersections between adjacent ones of the first and second surfaces may be filleted or rounded. Curved first and second surfaces 162, 164 and/or rounded intersections between adjacent first and second surfaces may allow the profile of the plurality of ridges 158 to match the profile of the corrugations 116 on the lateral edges of the body 82 of the cushion 24.

In some examples, the plurality of ridges 158 may be integrally molded onto the interior surfaces 154, 156. In some examples, the plurality of ridges may be molded onto separate inserts that may be mounted to or on the interior surfaces 154, 156 prior to insertion of the cushion 24 into the passage 30. Provision of separate inserts that include the plurality of ridges molded thereon may permit ridges that have a more prominent and/or undercut configuration.

It is believed that the disclosure set forth herein encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the disclosure includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

We claim:

1. A dental instrument servicing system, comprising:
a holder having a passage extending from a first opening to a second opening that is smaller than the first opening, the first and second openings being sized to receive portions of a cushion; and
a cushion having a first portion received within the passage, a second portion extending from the first portion through and beyond the second opening, a third portion extending from the first portion opposite the second portion outside the passage of the holder beyond the first opening, first and second spaced-apart surfaces, and a peripheral surface extending between the first and second surfaces, the peripheral surface including opposing sides generally tapering from the third portion to the second portion, the cushion having a discontinuous neck when the cushion is uncompressed, the neck adjacent a transition from the first portion to the second portion; and
wherein the peripheral surface includes opposing ridges extending transversely to the first and second surfaces, outside the passage adjacent the second opening of the holder when the first portion of the cushion is received within the passage with the second portion of the cushion extending beyond the second opening, the ridges not extending across the first and second surfaces, wherein the second portion of the cushion extending beyond the second opening is of a larger size than the second opening.

2. The dental instrument servicing system of claim 1, wherein the second opening, disposed on the holder opposite the first opening, has an edge, the ridge engages the edge when the first portion of the cushion is received within the passage and the second portion of the cushion extends beyond the second opening, and engagement of the ridge with the edge of the second opening provides an indication that the first portion of the cushion is properly received within the passage.

3. The dental instrument servicing system of claim 1, wherein the second opening, disposed below the first opening at a bottom of the holder, has first and second opposed edge sections, the opposinq ridges of the cushion engaging respective ones of the first and second opposed edge sections of the holder when the first portion of the cushion is received within the passage with the second portion of the cushion extending beyond the second opening.

4. The dental instrument servicing system of claim 3, wherein engagement between the opposing ridges and respective ones of the first and second opposed edge sections of the holder at least partially impedes removal of the cushion from the passage.

5. The dental instrument servicing system of claim 3, wherein the opposing ridges of the cushion provide the transition between the first and second portions of the cushion.

6. The dental instrument servicing system of claim 1, where prior to the first portion of the cushion being received within the passage the first and second surfaces are parallel and the ridge extends substantially perpendicularly to the first and second surfaces.

7. The dental instrument servicing system of claim 1, wherein the peripheral surface of the cushion includes corrugations extending transversely to the first and second surfaces around most of the peripheral surface, and the opposing ridges are larger than the corrugations.

8. The dental instrument servicing system of claim 7, wherein the corrugations are distributed around substantially the entire peripheral surface of the cushion.

9. The dental instrument servicing system of claim 1, wherein the holder includes at least one interior surface defining at least a portion of the passage, the passage extends from the first opening to the second opening along an axis, and the interior surface of the holder includes a plurality of ridges extending generally transversely to the axis.

10. The dental instrument servicing system of claim 1, wherein the cushion comprises an open-cell foam.

11. The system of claim 1, wherein the second opening has an inner perimeter and the second portion has an outer perimeter that is larger than the inner perimeter when the cushion is in the received position.

12. The system of claim 1, wherein the second portion includes a portion that is biased against removal through the second opening when the cushion is received within the passage.

* * * * *